United States Patent [19]

Sweeney

[11] Patent Number: 5,496,288

[45] Date of Patent: Mar. 5, 1996

[54] PROTECTIVE CAP FOR HYPODERMIC SYRINGE

[75] Inventor: Niall Sweeney, Rutherford, N.J.

[73] Assignee: Becton, Dickinson and Company, Franklin Lakes, N.J.

[21] Appl. No.: 950,113

[22] Filed: Sep. 23, 1992

[51] Int. Cl.⁶ .................................................. A61B 19/00
[52] U.S. Cl. ........................... 604/263; 604/403; 220/254
[58] Field of Search ..................................... 604/187, 238, 604/263, 403; 220/254, 337, 339

[56] References Cited

U.S. PATENT DOCUMENTS

| | | | |
|---|---|---|---|
| 4,494,679 | 1/1985 | Cleevely | 220/254 X |
| 4,613,326 | 9/1986 | Szwarc | 604/238 X |
| 4,693,708 | 9/1987 | Wanderer et al. | 604/263 X |
| 4,711,363 | 12/1987 | Marino | 220/254 X |
| 4,738,376 | 4/1988 | Markus | 220/254 X |
| 4,883,483 | 11/1989 | Lindmayer | 604/411 |
| 4,944,736 | 7/1990 | Holtz | 604/403 |
| 5,005,721 | 4/1991 | Jordan | 220/339 X |

FOREIGN PATENT DOCUMENTS

| | | | |
|---|---|---|---|
| 2224309 | 5/1990 | United Kingdom | 220/339 |
| 84/01291 | 4/1984 | WIPO | 604/187 |

*Primary Examiner*—Sam Rimell
*Attorney, Agent, or Firm*—John L. Voellmicke

[57] ABSTRACT

A protective cap is provided for a hypodermic syringe. The protective cap is hingedly connected to the distal end of the hypodermic syringe for rotation relative thereto. In a first rotational orientation the protective cap sealingly engages a passageway extending through the distal end of the hypodermic syringe. In a second rotational orientation the protective cap enables complete access to the passageway extending through the distal end of the hypodermic syringe and into the chamber. The protective cap can be separately mounted to the hypodermic syringe or unitarily formed therewith. Preferably, the protective cap is configured to enable easy one-handed and opening and closure by a health care worker.

8 Claims, 5 Drawing Sheets

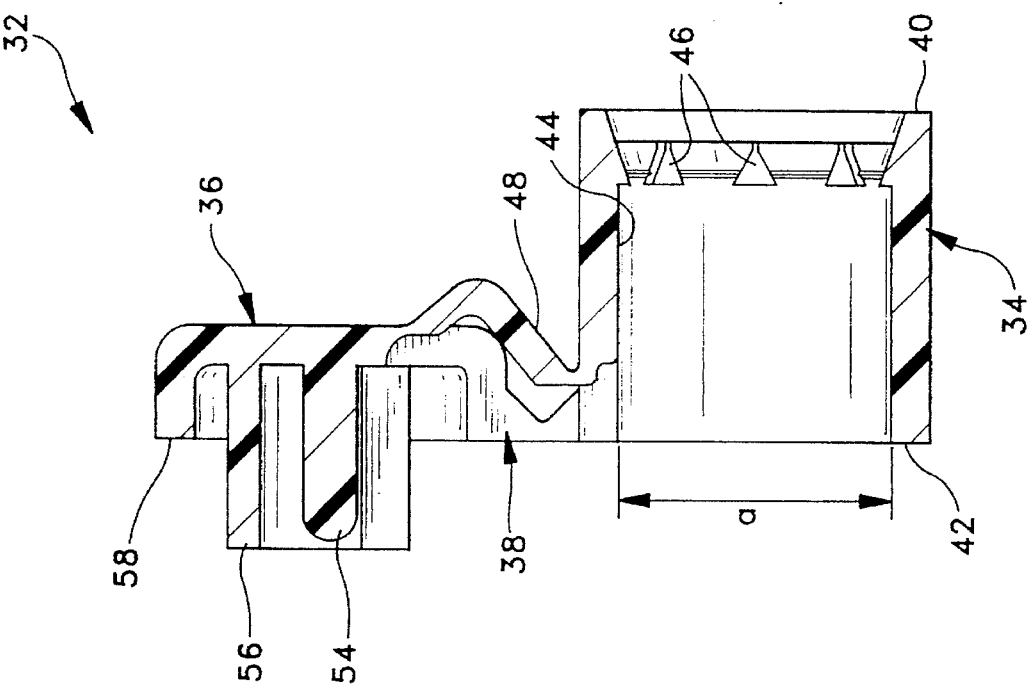
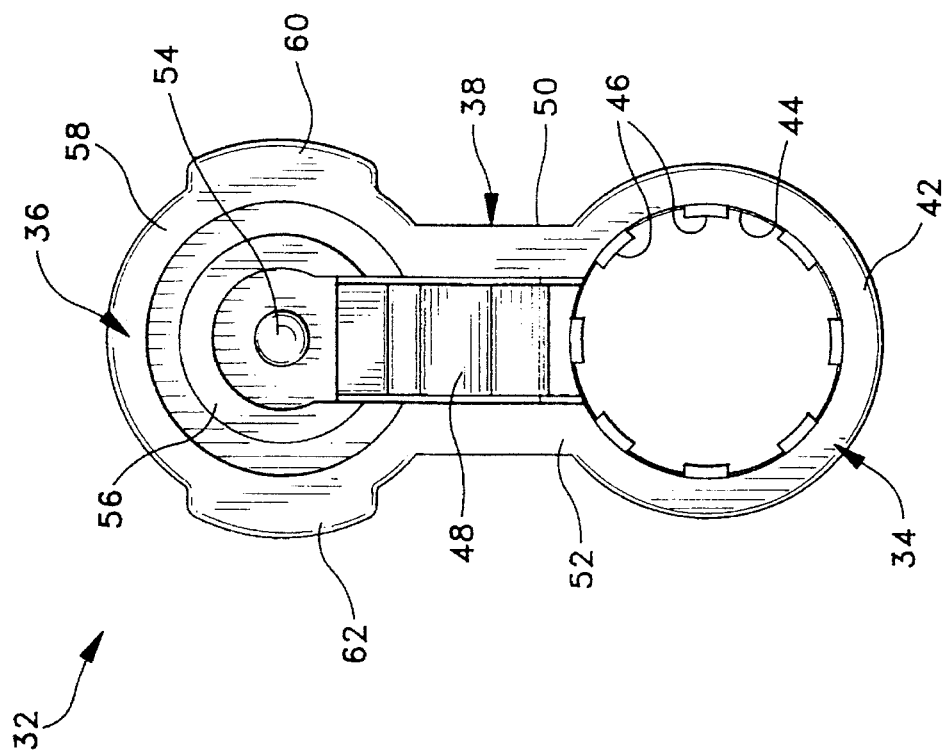

PROTECTIVE CAP FOR HYPODERMIC SYRINGE

FIELD OF THE INVENTION

The present invention relates to a protective cap for a hypodermic syringe, and more particularly to a protective cap that easily can be urged into or out of sealing engagement with a passageway at an end of a syringe barrel.

DESCRIPTION OF THE PRIOR ART

A typical prior art hypodermic syringe includes a cylindrical barrel having an open proximal end, a distal end and a fluid-receiving chamber therebetween. The distal end of the syringe barrel includes a passageway extending therethrough and communicating with the chamber. A plunger is slidably disposed in the chamber and is in fluid-tight engagement with the walls of the syringe barrel. Movement of the plunger toward the distal end of the syringe barrel urges fluid in the chamber through the passageway at the distal end of the syringe barrel. Conversely, movement of the plunger away from the distal end of the syringe barrel draws fluid through the passageway and into the chamber.

The construction of the distal end of the prior art hypodermic syringe may vary considerably. For example, some prior art hypodermic syringes are adapted to receive a sharp metallic needle cannula which can be injected into a patient or into a tube. The syringe containing fluids may be stored and transported without the needle cannula to minimize storage space and eliminate the chance of an accidental needle stick while allowing the user to choose the appropriate needle size at the time of use.

Other prior art hypodermic syringes include a cannula with a blunt tip that substantially prevents accidental puncture wounds. The blunt tip may be a unitary part of the syringe barrel or may define a short thermoplastic tubular member that is threadedly and/or frictionally engageable to the distal end of the syringe barrel.

Prior art hypodermic syringes may have a fluid placed in the chamber of the syringe barrel at a pharmacy in a health care facility. The filled hypodermic syringe barrel may then be transported from the pharmacy to an appropriate location in the health care facility where a health care employee will inject the fluid. The distal end of the hypodermic syringe preferably should be sealed to avoid contamination and to prevent leakage between the pharmacy and the patient.

Some prior art hypodermic syringes may also be used to draw a fluid from the patient or from a tube communicating with the patient for subsequent laboratory analysis. Once again, the distal end of the syringe must be sealed during transportation from the patient to the laboratory to prevent leakage and to avoid contamination.

In still other instances, a syringe without a sharp needle may be used to flush lines on laboratory equipment through luer slip and locking luer fittings which engage the distal tip of the syringe barrel or to deliver medication or other fluid by piercing a pre-slit septum in an intravenous access line. For example, a prior art hypodermic syringe may be used to clean a line of a kidney dialysis machine by drawing blood and saline from a tube of the dialysis machine. Although the fluid withdrawn in this manner does not require reuse or analysis, it is necessary to prevent the fluid from leaking into contact with nearby equipment or personnel. Hence, it is desirable to seal the distal end of the prior art hypodermic syringe that is used to flush or clean lines of medical equipment.

Still other prior art hypodermic syringes may be used to administer anesthesia intermittently through a stopcock of an intravenous line. Once again, it is important to seal the distal end of the prior art syringe between the intermittent administrations of the anesthesia.

Prior art hypodermic syringes have included separate caps that can be releasably engaged to the distal end of the syringe barrel for sealing the passageway to the chamber of the barrel. A separate cap can easily become lost and creates inventory control problems. Additionally, a separate cap requires the health care worker to use both hands to mount the cap onto the hypodermic syringe barrel or to remove the cap therefrom. The realities of a hectic health care facility often prevent health care workers from having two free hands to separate the cap from the syringe barrel and to place the separated cap at a location for convenient subsequent access. Similarly, the health care worker often will not have two hands available for retrieving a separate cap and remounting the cap to the distal end of the hypodermic syringe. Rather than fumbling with a separate cap, a worker may be compelled to leave the syringe unprotected. Also, loose caps represent a separate item that must be accounted for in certain procedures where loose elements may constitute a health hazard. Hence, despite the desirability of employing a protective cap, many prior art hypodermic syringes may not be protectively sealed.

The prior art has included flexible straps to join a protective cap to a component intended for use with a hypodermic syringe. A flexible strap may prevent the cap from becoming lost. However, a flexible strap still requires two-handed manipulation to engage or disengage the cap from the structure to which the cap is connectable. Examples of caps connected by flexible straps are shown in U.S. Pat. No. 4,883,483 to Lindmayer and U.S. Pat. No. 4,944,736 to Holtz. Both of these prior patents show adapters mountable to bottles which can be placed in communication with hypodermic syringes.

Neither of these patents, however, show caps mountable to the hypodermic syringe itself.

SUMMARY OF THE INVENTION

The subject invention is directed to a protective cap for a hypodermic syringe. The protective cap of the subject invention includes a cover hingedly disposed in proximity to an end of a syringe barrel. The cover of the protective cap may be hingedly rotatable about an axis extending substantially perpendicular to the longitudinal axis of the syringe barrel.

The protective cap preferably is constructed to enable easy manipulation of the cover and the hypodermic syringe with one hand. In particular, the protective cap may be constructed to enable a user to flip the cover from a fully closed position to a fully opened position with one finger, or to move the cover from a fully opened position to a fully closed position with one finger. Thus, a health care worker who may be holding a patient or medical instrument with one hand can, for example in a needleless application, use the other hand to remove the protective cap, administer a partial dose of medicine, and then conveniently urge the cover of the protective cap into a position for positively sealing the passageway through the distal end of the syringe barrel.

The protective cap may be unitarily formed with the syringe barrel. Alternatively, the cover and the hinge may be unitarily molded to a collar frictionally mechanically or adhesively engageable on the tip of the syringe barrel. The mode of engagement of the collar to the syringe barrel can be permanent or removable.

The cover of the protective cap may include a inner sealing face for positive engagement with portions of the hypodermic syringe barrel defining the passageway. For example, the protective cap may include a projection dimensioned for sealing engagement in the passageway. Additionally, or alternatively, the inner face of the protective cap may be configured and dimensioned to telescope over the tip of the syringe barrel. External regions of the protective cap may be provided with access tabs to facilitate engagement by a thumb or forefinger for selectively flipping the cover of the protective cap into a position where the passageway is conveniently and completely accessible.

BRIEF DESCRIPTION OF THE DRAWINGS

FIG. 4 is a top plan view of a unitarily formed collar and protective cap for mounting on a hypodermic syringe;

FIG. 5 is a cross-sectional view taken along line 5—5 in FIG. 4; and

DETAILED DESCRIPTION OF THE PREFERRED EMBODIMENT

Figure 1:
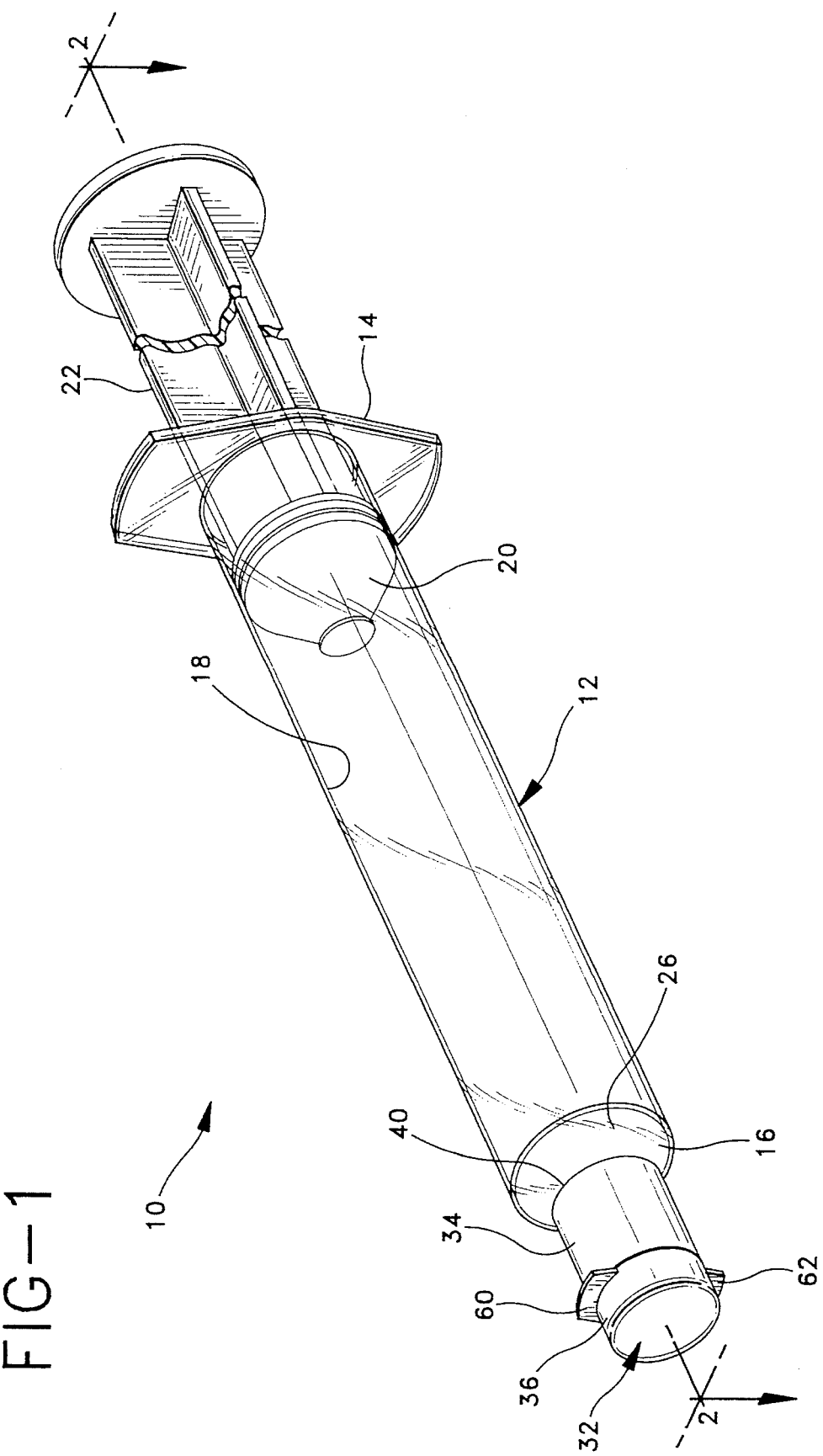
FIG. 1 is a side elevational view of a hypodermic syringe with the protective cap of the subject invention.
Figure 2:
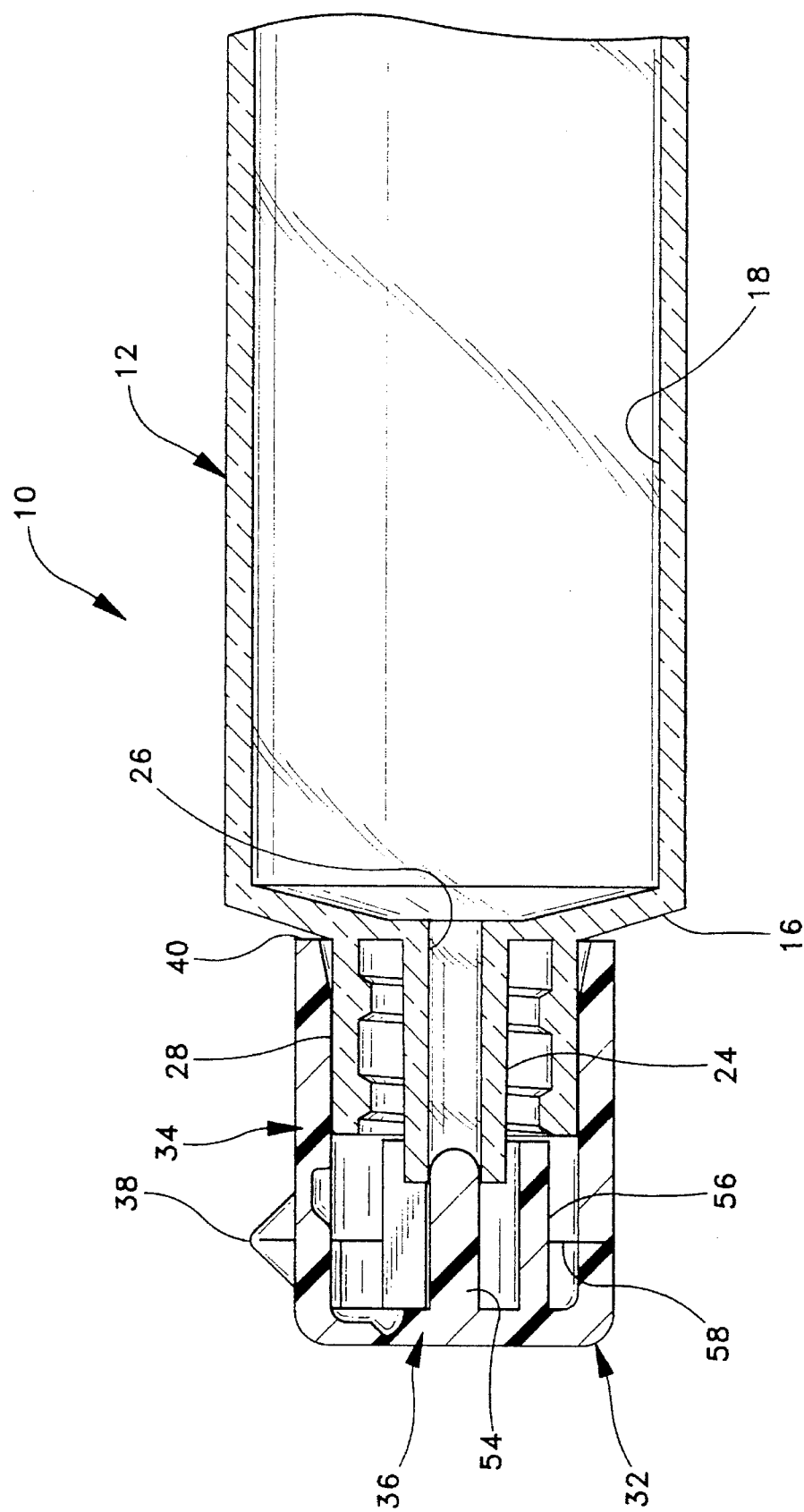
FIG. 2 is an enlarged cross-sectional view taken along line 2—2 in FIG. 1.
Figure 3:
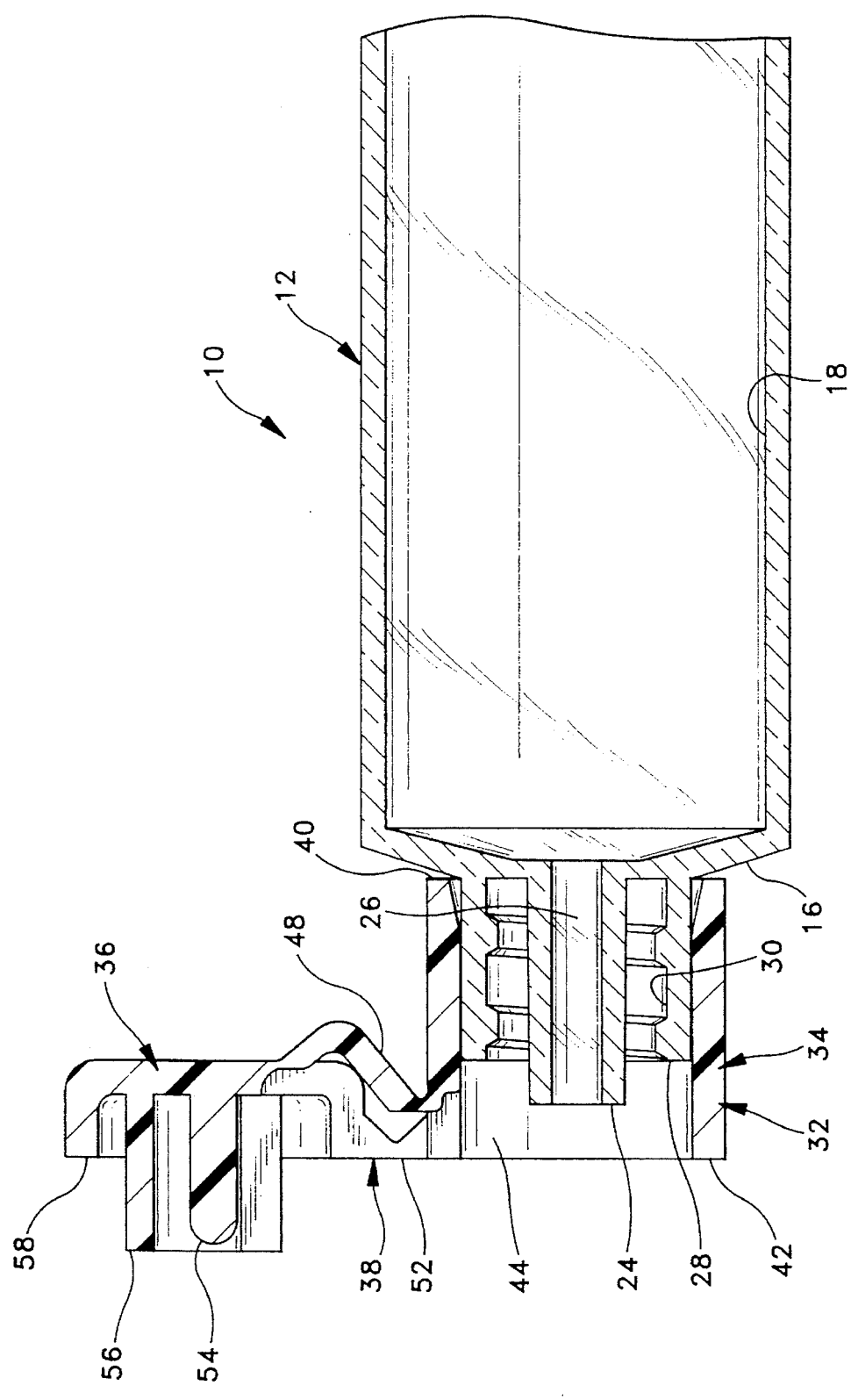
FIG. 3 is a cross-sectional view similar to FIG. 2 but showing the protective cap in an open condition.

A hypodermic syringe in accordance with the subject invention is identified generally by the numeral 10 in FIGS. 1–3. The hypodermic syringe includes a generally cylindrical barrel 12 having an open proximal end 14, a distal end 16 and a fluid-receiving chamber 18 extending therebetween. A stopper 20 is slidably disposed in fluid-tight engagement inside the barrel. A plunger rod 22 extends rigidly from stopper 20 and projects beyond the open proximal end of the syringe barrel.

The distal end of syringe barrel 12 includes a tip 24 having a passageway 26 extending axially therethrough and communicating with the chamber of syringe barrel 12. A generally cylindrical sleeve 28 is positioned at distal end 16 of syringe barrel 12 in concentric spaced relationship to syringe tip 24, such an annular space 30 exists between syringe tip 24 and sleeve 28. Cylindrical sleeve 28 is provided with an array of internal threads (not shown) for receiving the hub of a blunt cannula or a needle cannula.

To prevent leakage of fluid from chamber 18 and/or to prevent contamination of fluid in chamber 18 from the environment, the distal end of syringe barrel 12 is provided with a protective cap identified generally by the numeral 32 in FIGS. 1–5. As shown most clearly in FIGS. 2–5, protective cap 32 includes a generally cylindrical collar 34 and a cover 36 unitarily connected to collar 34 by a hinge 38. Collar 34 has opposed proximal and distal ends 40 and 42 respectively and a generally cylindrical inner surface 44 extending therebetween. The cylindrical inner surface of collar 34 defines an inside diameter "a" which is substantially equal to or slightly less than the outside diameter of sleeve 28 on the distal end of syringe barrel 12. Inner cylindrical surface 44 is flared slightly outwardly adjacent the proximal end of collar 34 to facilitate alignment and subsequent mounting of collar 34 over sleeve 28 at the distal end of syringe barrel 12.

The inner surface of collar 34 is further characterized by at least one end preferably a plurality of locking barbs 46 projecting generally radially inwardly adjacent the outwardly flared portion at the proximal end of the collar. The projection of the barbs from inner surface 44 increases at greater distances from proximal end 40 of the collar. With this configuration, barbs 46 will bite into the outer cylindrical surface of sleeve 28 as the proximal end of collar 34 is telescoped in a proximal direction over the outer cylindrical surface of sleeve 28 on the syringe barrel. This configuration of barbs 46 will substantially prevent movement of collar 34 in a distal direction.

Hinge 38 is configured to urge cover 36 into either a fully closed rotational orientation, as shown in FIGS. 1 and 2 or a fully opened rotational orientation as depicted in FIGS. 3–5. More particularly, as shown most clearly in FIG. 4, hinge 38 includes a center hinge 48 disposed intermediate biasing hinges 50 and 52 respectively. As shown most clearly in FIGS. 3 and 5, center hinge 48 is configured to rotate about an axis that is substantially perpendicular to the axis of the syringe barrel and offset from the rotational axes of biasing hinges 50 and 52. In operation, biasing hinges 50 and 52 will be stretched or biased at rotational orientations between the fully closed condition shown in FIGS. 1 and 2 and the fully opened condition shown in FIGS. 3–5. This biasing of hinges 50 and 52 combined with the inherent resiliency of the thermoplastic material from which protective cap 32 is molded causes the biasing hinges 50 and 52 to urge cover 36 toward either the fully opened position or the fully closed position. As a result, the cover 36 effectively can be snapped into an opened position or into a closed position by a health care employee using only one hand.

In this embodiment it is preferred that collar 34, hinge 38 and cover 36 are formed in a unitary or integral structure of the same material, such as by injection molding into a unitary structure of thermoplastic material such as polypropylene.

Cover 36 of the protective cap includes a center projection or pin 54 disposed and dimensioned to telescope into passageway 26 formed in the distal end of syringe barrel 12. Cover 36 further includes an outer projection 56 disposed and dimensioned to telescope over tip 24 at the distal end of syringe barrel 12. The outer projection in this embodiment is of incomplete cylindrical shape and is concentric with inner projection 54. More particularly, cylindrical projection 56 is discontinuous in regions aligned with center hinge 48. This discontinuity enables the cover to hingedly rotate relative to collar 34 and to snap directly into a sealed engagement with the tip of syringe barrel 12.

Cover 36 further includes an outer collar portion 58 dimensioned and configured to register with collar 34 in the fully closed condition of cover 36 as depicted in FIGS. 1 and 2. Thus, cover 36 provides for multiplied sealing over the distal end of syringe barrel 12, including the telescoping of center projection 54 into passageway 26, the telescoping outer projection 56 over tip 24 and the registration of collar portion 36 of the cap with the distal end of collar 34. It is preferred that the center projection or pin 54 be recessed with respect to outer projection 56 to help prevent accidental contamination of the pin and therefore to help prevent contamination of passageway 26.

As illustrated most clearly in FIGS. 1 and 4, cover 36 of the protective cap is provided with a pair of tabs 60 and 62 which project outwardly from the collar of cover 36. The tabs are dimensioned to facilitate contact with the thumb or forefinger of the health care employee working with hypodermic syringe 10 to facilitate one-handed opening.

Figure 6:
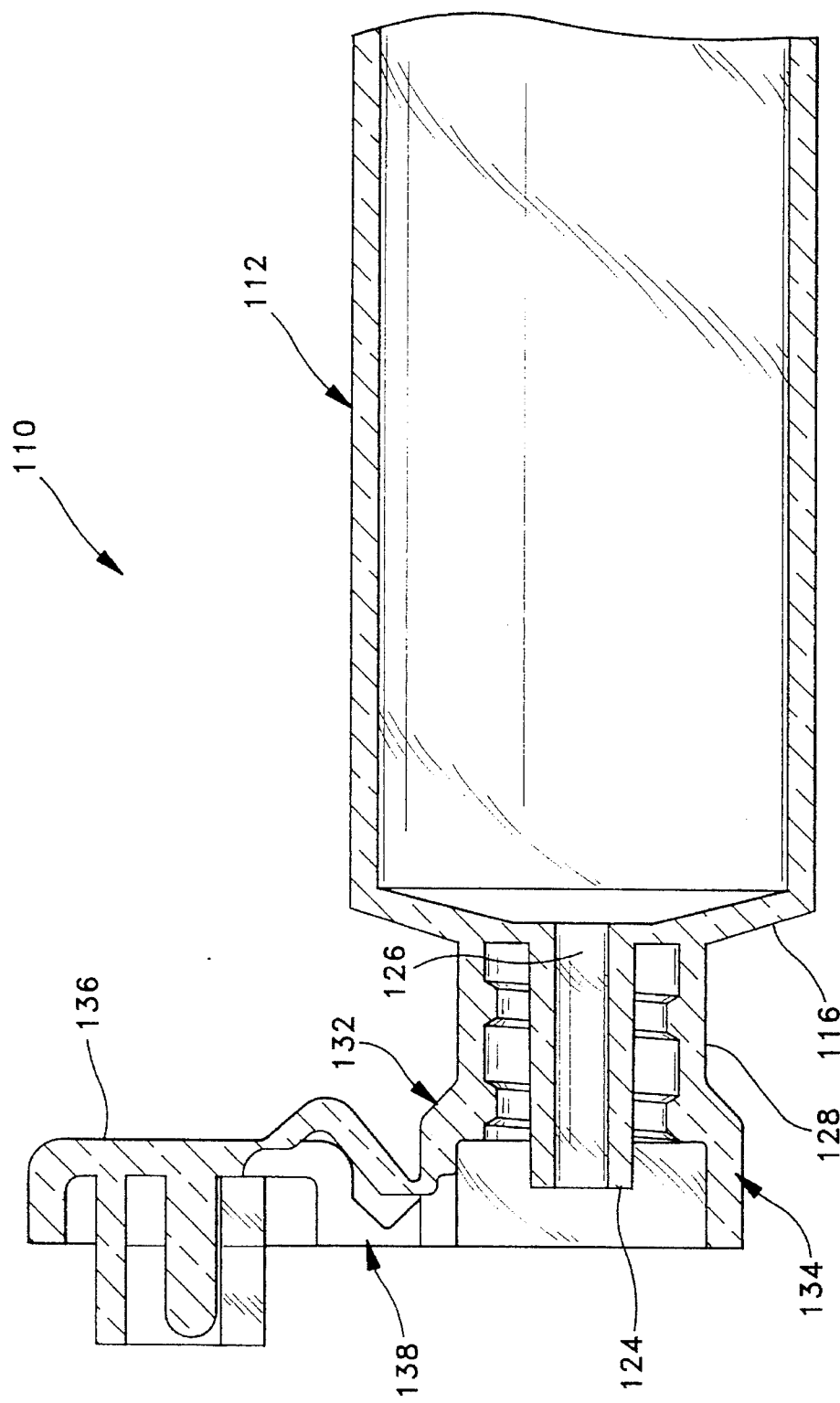
FIG. 6 is a cross-sectional view similar to FIG. 3, but showing an alternate protective cap.

An alternate syringe is identified generally by the numeral 110 FIG. 6. The syringe 110 includes a syringe barrel 112 similar to syringe barrel 12 described and illustrated above. Syringe barrel 112 is characterized by a distal end 116 having a tip 124 with a passageway 126 extending therethrough. A cylindrical sleeve 128 surrounds tip 124 in concentric spaced relationship. A protective cap identified generally by the numeral 132, is connected to sleeve 128 of syringe barrel 112. The protective cap includes a hinge 138 joined to sleeve 128, and a cover 136 joined to the hinge. Hinge 138 and cover 136 illustrated in FIG. 6 are substantially the same as hinge 38 and cover 36 described and illustrated above. The cover and the hinge are preferably integrally or unitarily formed with the syringe barrel.

Syringe 110 differs from the syringe considered in the previous embodiment in that hinge 138 is connected directly to syringe barrel 112 and not to a collar. Thus, it is unnecessary to provide a separate cap as in FIGS. 4 and 5 for mounting over the distal end of a syringe barrel. In all other respects, however, the protective cap 132 functions similar to protective cap 32 illustrated in FIGS. 1–5. In particular, protective cap 132 provides efficient one-handed covering and one-handed opening of the distal end of syringe barrel 112 by a health care worker.

What is claimed is:

1. A hypodermic syringe barrel having a protective cap comprising: a syringe barrel having a distal end, a chamber wall adjacent the distal end defining a cylindrical fluid-receiving chamber and a longitudinal axis, said distal end of said syringe barrel having a fluid passageway extending therethrough and communicating with said chamber;

said protective cap including a generally tubular collar having opposed proximal and distal ends and an inner surface extending therebetween, said inner surface being dimensioned and configured for fixed retention on said distal end of said syringe barrel;

a hinge extending from said collar; and a cover joined to said hinge for rotation about an axis substantially perpendicular to said longitudinal axis of said syringe barrel between an open position where said cover is spaced from said syringe barrel and a closed position where said cover protectively covers said distal end of said syringe barrel, said cover including an inner face having at least one projection for sealing engagement with said distal end of said syringe barrel, said projection comprising an elongate center projection sealingly engageable in said passageway at said distal end of said syringe barrel.

2. The syringe barrel of claim 1, wherein said cover further comprises an outer projection for sealing engagement around at least a portion of said distal end of said syringe barrel.

3. The syringe barrel of claim 2, wherein said outer projection is generally concentrically disposed around said center projection of said cover, said outer projection being discontinuous on portions aligned with said hinge to facilitate hinged rotation of said cover between said open and said closed positions.

4. A hypodermic syringe barrel having a protective cap comprising:

said barrel having a distal end, a chamber wall extending proximally from said distal end, said chamber wall defining a chamber and a longitudinal axis, said distal end of the syringe barrel comprising a tip having a passageway extending therethrough and in fluid communication with said chamber, a sleeve rigidly disposed at said distal end of said syringe barrel in concentric spaced relation around said tip;

said protective cap including a generally cylindrical collar having opposed proximal and distal ends and a generally cylindrical inner surface extending therebetween, said inner surface including engagement means for fixedly attaching said cylindrical collar on said sleeve of said syringe barrel;

a hinge unitarily formed at said distal end of said collar, said hinge defining a rotational axis substantially perpendicular to said longitudinal axis of said syringe barrel; and a cover unitary with said hinge for rotation between an open position where said cover is spaced from said syringe barrel to a closed position where said cover seals said passageway through said tip from the environment.

5. The syringe barrel of claim 4, wherein said cover includes a center projection disposed and dimensioned for sealing engagement in said passageway of said tip and an outer projection dimensioned and disposed for sealing engagement with said tip between said tip and said sleeve at said distal end of said syringe barrel.

6. The syringe barrel of claim 5, wherein said outer projection defines a segment of a cylinder having a discontinuity on portions thereof aligned with said hinge to enable rotation of aid cover about said hinge between said open position and said closed position.

7. A hypodermic syringe barrel comprising:

a distal end, a chamber wall extending from said distal end, said chamber wall defining a cylindrical chamber and a longitudinal axis, said distal end of said syringe barrel including an elongate tip aligned with said longitudinal axis having a passageway extending therethrough and communicating with said chamber, said distal end further including a sleeve unitary therewith and disposed in spaced concentric relationship around said tip, a cover connected by a hinge to said sleeve for rotation about an axis substantially perpendicular to said longitudinal axis of said syringe barrel, said cover having at least one projection being disposed and dimensioned for sealing engagement in said passageway.

8. A hypodermic syringe barrel having a protective cap comprising:

a syringe barrel having a distal end, a chamber wall adjacent the distal end defining a cylindrical fluid-receiving chamber and a longitudinal axis, said distal end of said syringe barrel having a fluid passageway extending therethrough and communicating with said chamber;

said protective cap including a generally tubular collar having opposed proximal and distal ends and an inner surface extending therebetween, said inner surface being dimensioned and configured for fixed retention on said distal end of said syringe barrel;

a hinge extending from said collar; and a cover joined to said hinge for rotation about an axis substantially perpendicular to said longitudinal axis of said syringe barrel between an open position where said cover is spaced from said syringe barrel and a closed position where said cover protectively covers said distal end of said syringe barrel, said hinge of said protective cap including biasing means for urging said cover into either of said open or said closed positions relative to said collar.

* * * * *